US009731038B2

(12) United States Patent
Turner (10) Patent No.: US 9,731,038 B2
(45) Date of Patent: Aug. 15, 2017

(54) NASAL CANULA COVER (71) Applicant: Charles Andrew Turner, Orefield, PA (US)

(72) Inventor: Charles Andrew Turner, Orefield, PA (US)

( * ) Notice: Subject to any disclaimer, the term of this patent is extended or adjusted under 35 U.S.C. 154(b) by 367 days.

(21) Appl. No.: 14/543,541

(22) Filed: Nov. 17, 2014

(65) Prior Publication Data

US 2015/0068928 A1  Mar. 12, 2015

Related U.S. Application Data (63) Continuation-in-part of application No. 12/126,293, filed on May 23, 2008, now Pat. No. 8,887,919.

(51) Int. Cl.
*A61L 2/10* (2006.01)
*A61B 50/00* (2016.01)
*A61M 16/06* (2006.01)
*A61B 50/30* (2016.01)

(52) U.S. Cl.
CPC ............. *A61L 2/10* (2013.01); *A61B 50/00* (2016.02); *A61M 16/0666* (2013.01); *A61B 2050/0054* (2016.02); *A61M 2205/11* (2013.01); *A61M 2209/06* (2013.01)

(58) Field of Classification Search
CPC ... A61L 2/10; A61B 50/00; A61B 2050/0054; A61M 16/0666; A61M 2205/11; A61M 2209/06
See application file for complete search history.

(56) References Cited

U.S. PATENT DOCUMENTS

| | | | | |
|---|---|---|---|---|
| 4,818,320 A | * | 4/1989 | Weichselbaum .. | A61M 16/0666 128/207.18 |
| D612,148 S | * | 3/2010 | Treece ......................... | D3/203.1 |
| 7,798,332 B1 | * | 9/2010 | Brunet .............. | A61M 16/0666 206/364 |
| 2007/0027375 A1 | * | 2/2007 | Melker ................ | A61B 5/0873 600/340 |
| 2009/0199858 A1 | * | 8/2009 | Hagberg ........... | A61M 16/0666 128/207.18 |

FOREIGN PATENT DOCUMENTS

CH              699918 B1 *  5/2010  ............. A45C 11/00

* cited by examiner

*Primary Examiner* — Sundhara Ganesan
(74) *Attorney, Agent, or Firm* — Lyman Smith (57) ABSTRACT

A protective cover for a nasal cannula completely encloses the two prongs of the nasal cannula when properly installed. This protective cover will keep the nasal cannula from contacting potentially unclean surfaces when the nasal cannula is not in use. An optional UV light may be present in the protective cover to provide UV cleaning of the nasal cannula prongs when the cover is closed.

12 Claims, 11 Drawing Sheets

NASAL CANULA COVER

CROSS-REFERENCE TO RELATED APPLICATION

This application is a continuation-in-part of U.S. patent application Ser. No. 12/126,293, filed May 23, 2008, currently pending, the contents of which are herein incorporated by reference.

BACKGROUND OF THE INVENTION

The present invention relates to delivery systems for patients taking oxygen or other fluids or gases through a nasal cannula. More specifically, the present invention relates to a protective storage of the nasal cannula while not in use.

It is known that a nasal cannula is a device used to deliver supplemental oxygen to a person through the nostrils. This device consists of a plastic tube, connected to an oxygen source, and a set of two prongs which engage the nostrils of the wearer. Oxygen is delivered through holes in the prongs. The tubing is kept in place by fitting it around the patient's ears.

Nasal cannulas are manufactured and transported in clean conditions so as to keep the area of the prongs clean. Standard operating procedure among medical professionals dictates that when a nasal cannula comes in contact with any unclean or unsanitary surface, it must be discarded. It is also known that to keep the nasal cannula from becoming soiled when not in use, the wearer or caregiver will typically hang it on a bed post or hook. Unfortunately, the natural coiling and uncoiling properties of the plastic tube can cause it to fall even when it appears to be safely secured.

A number of accessory devices for use with nasal cannulas have been proposed. By way of example, Published U.S. Patent Application 2007/0270736 to Giarrocco-Brettner shows bulb syringe improvement. The device partially covers a nasally inserted portion of the bulb syringe. In addition, it prevents contact between the nasally inserted portion of the bulb syringe and an unclean table surface. The device does not, however, provide full coverage over a two prong nasal cannula.

In addition, a number of other accessories for nasal cannulas are shown in the art. For example, U.S. Pat. No. 6,026,811 to Settle shows a protective cover for the tubing of a nasal cannula which provides comfort for the patient's ear. Published U.S. Patent Application 2005/0236001 to Williams shows a bridle system which clamps around the tubes exiting a patient's nose. However, the prior art does not show a cover for use in protecting the nasal cannula.

As can be seen, there is a need for a device that protects a nasal cannula from becoming soiled while not in use.

SUMMARY OF THE INVENTION

In one aspect of the present invention, a method for protecting prongs of a nasal cannula when not in use comprises placing the prongs of the nasal cannula into a space inside a nasal cannula cover; directing nasal cannula tubing into openings formed on opposite sides of the nasal cannula cover; and closing the nasal cannula cover to secure the prongs within the space.

In another aspect of the present invention, a nasal cannula cover comprises a top member; a bottom member hingedly connected to the top member; an enclosed space disposed inside the top member and bottom member when the top member is closed against the bottom member; a plurality of rib slots disposed inside top member and the bottom member; and ribs disposed in corresponding ones of the plurality of rib slots in the top member and the bottom member on each side of the nasal cannula cover.

In a further aspect of the present invention, a nasal cannula cover comprises an enclosed space receiving nasal cannula prongs of a nasal cannula; and a rotation limiting device inside the enclosed space preventing the nasal cannula prongs from touching an inside surface of the nasal cannula cover.

The present invention relates to a protective cover for a nasal cannula. The device can completely enclose the two prongs of the nasal cannula when properly installed. This protective cover can keep the nasal cannula from contacting the floor, bed sheets, or other potentially unclean surfaces when the nasal cannula is not in use. Multiple embodiments are described. Generally, the device includes two components which are pivotally attached together. The hinge can be of any type, for instance, a living hinge or a pinned hinge, and optionally the two halves may be biased toward each other or away from each other, for instance, by a spring.

In one embodiment, the two halves are substantially similar to each other, and both are clamshell shaped. The interior of the clamshell shaped covers contain a fixturing rib for contacting the two sides of the nasal cannula base tube. In operation, the patient need only place the cannula base tube on the fixturing rib of the bottom cover half. The patient can then close the other cover, which will secure the cannula base tube without contacting the cone shaped prongs—which are the nasally inserted portions.

In another embodiment, the first half is elongated to match the side profile shape of the nasal cannula. The patient need only insert the cone shaped prongs into the first half. The first half has a base tube opening with half-moon shaped clips. The half-moon shaped clips attach to the cannula base tube. Finally, a hinge attached door is closed to seal the nasal cannula.

In another embodiment, the cover includes two shells which when closed form an interior cylinder. When closed around the nasal cannula, the cover may rotate 360 degrees around the axis of the cannula base tube. While rotating the cover, no part of the nasally inserted cannula can touch any part of the interior cylinder. In addition, the barrel cover contains two feed tube locators which abut against the cannula feed tube shoulder, and prevent lateral sliding of the barrel cover.

All embodiments of the present invention can include leg protrusions which provide stability against rolling on horizontal surfaces.

There has thus been outlined some features of the invention in order that the detailed description thereof that follows may be better understood, and in order that the present contribution to the art may be better appreciated. There are additional features of the invention that will be described hereinafter and which will form the subject matter of the claims appended hereto. In as much as the foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the disclosed specific methods and structures may be readily utilized as a basis for modifying or designing other structures for carrying out the same purposes of the present invention. It should be realized by those skilled in the art that such equivalent methods and structures do not depart from the spirit and scope of the invention as set forth in the appended claims.

Therefore, it is an object of the present invention to provide a nasal cannula cover which prevents the nasal cannula from contacting potentially unclean surfaces when properly installed.

Yet another object of the present invention to provide a nasal cannula cover which is lightweight, durable and inexpensive to manufacture.

It is a further object of the present invention to provide a nasal cannula cover that is maintained in a position for easy access by the user or health professional when not installed over the prongs of the cannula.

It is a further object of the invention to provide a cannula cover that is easy for the patient or health professional to install and remove from the prongs of the cannula.

It is a further object of the present invention to provide a cannula cover with interior surfaces that will not contact un-clean surfaces while in the un-installed state.

It is further object of the present invention to provide a cannula cover having a UV light source configured to irradiate the prongs of the nasal cannula when stored within the cannula cover.

It is a further object of the present invention to provide a method for using the herein described cannula cover to protect the prongs of a nasal cannula from contacting potentially unclean surfaces.

These and other features, aspects and advantages of the present invention will become better understood with reference to the following drawings, description and claims.

BRIEF DESCRIPTION OF THE DRAWINGS

FIG. 1b is a side view of the nasal cannula cover of FIG. 1a;

FIG. 1c top perspective view of a bottom shell of the nasal cannula cover of FIG. 1a;

FIG. 2b is a top perspective view of a reusable slide-on cover of the nasal cannula cover of FIG. 2a;

FIG. 3b is a top perspective view of the nasal cannula cover of FIG. 3a;

FIG. 5c is an exploded perspective view of the nasal cannula cover of FIG. 5a;

FIG. 7c is a perspective view illustrating a latch and hinge structure on the nasal cannula cover of FIG. 7a which also could be used on the nasal cannula cover of FIG. 6a;

FIG. 7d is a perspective view illustrating a rotation resistance structure on the nasal cannula cover of FIG. 7a which also could be used on the nasal cannula cover of FIG. 6a;

FIG. 8b is a cross-sectional view taken along line 8B-8B of FIG. 8a; and

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, an embodiment of the present invention provides a protective cover for a nasal cannula. The device completely encloses the two prongs of the nasal cannula when properly installed. This protective cover will keep the nasal cannula from contacting potentially unclean surfaces when the nasal cannula is not in use. An optional UV light may be present in the protective cover to provide UV cleaning of the nasal cannula prongs when the cover is closed.

Figure 1A:
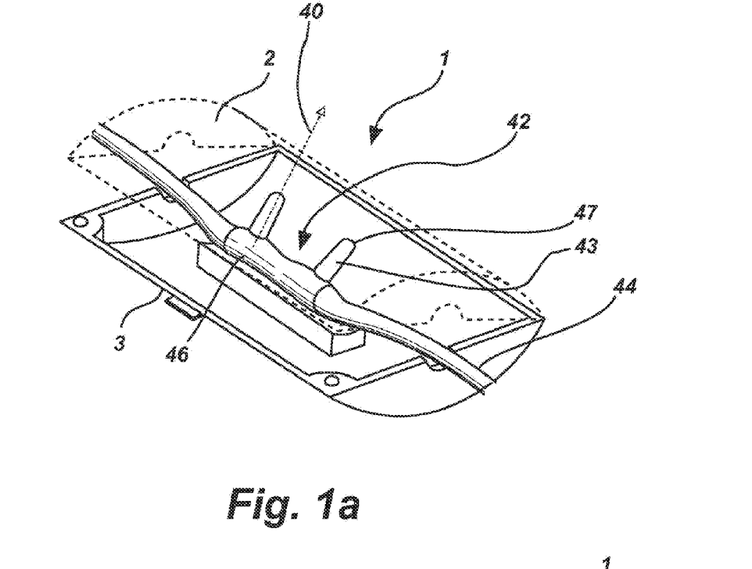
FIG. 1a is a top perspective view of a nasal cannula cover, with a nasal cannula placed therein, according to an exemplary embodiment of the present invention.
Figure 1B:
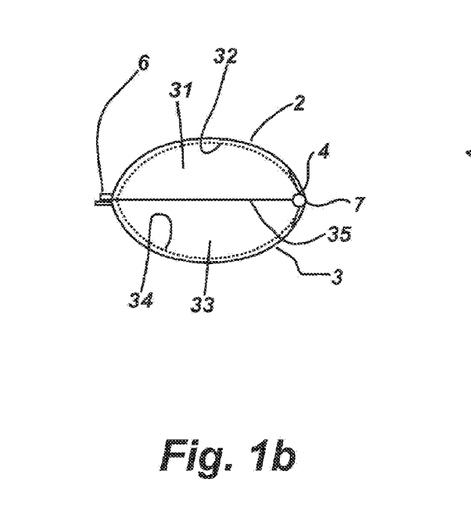
Figure 1C:
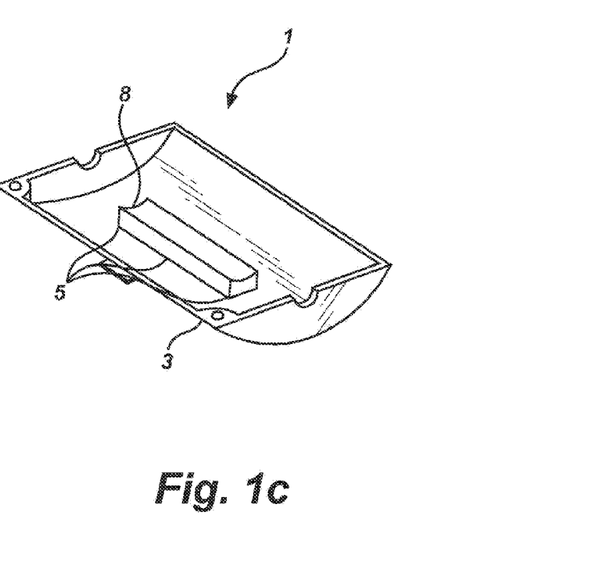

Referring now to FIGS. 1a through 1c, a clamshell cover 1, or a cover, is shown. A nasal cannula 42 is composed of a cannula base tube 46 (also referred to as prong base portion 46), and one or more cannula feed tubes 44, and one or more cone shaped prong 43. For reference, an axis 40 of the distal end of the cannula 42 is defined as the central longitudinal axis of the cone shaped prong 43. Also, the cone shaped prong 43 has a distal end 47. Typically, the nasal cannula 42 will include two cone shaped prongs 43, as shown in the Figures.

The clamshell cover 1 includes a top cover component 2 and a bottom cover component 3. The top cover component 2 has a first opening 31 in a bottom surface 32, and the bottom cover component 3 has a second opening 33 in a top surface 34. The top cover component 2 can contact the bottom cover component 3 at a mating 35.

The top cover component 2 is attached to the bottom cover component 3 by a hinge 7, or connecting member, which among other alternatives, can be of the known living hinge or pinned hinge types. Referring to FIG. 1b, the top cover component 2 is urged into contact with the bottom cover component 3 by a torsion spring 4, or biasing member. When in the closed position seen in FIG. 1b, a latch 6, or holding member, holds the top cover component 2 in contact with bottom cover component 3.

As seen in FIG. 1c, the bottom cover component 3 can include one or more base tube supports 5, or suspending member. The base tube support 5 contacts the cannula base tube 46 of the nasal cannula 42 when the nasal cannula 42 is inside the clamshell cover 1. As seen, the base tube support 5 has a semi-circular prong top 8 which conforms to the shape of the cannula base tube 46. In addition, the base tube support 5 is attached to both the top cover component 2 and the bottom cover component 3, which provides for two contact surfaces on the cannula base tube 46.

Figure 2A:
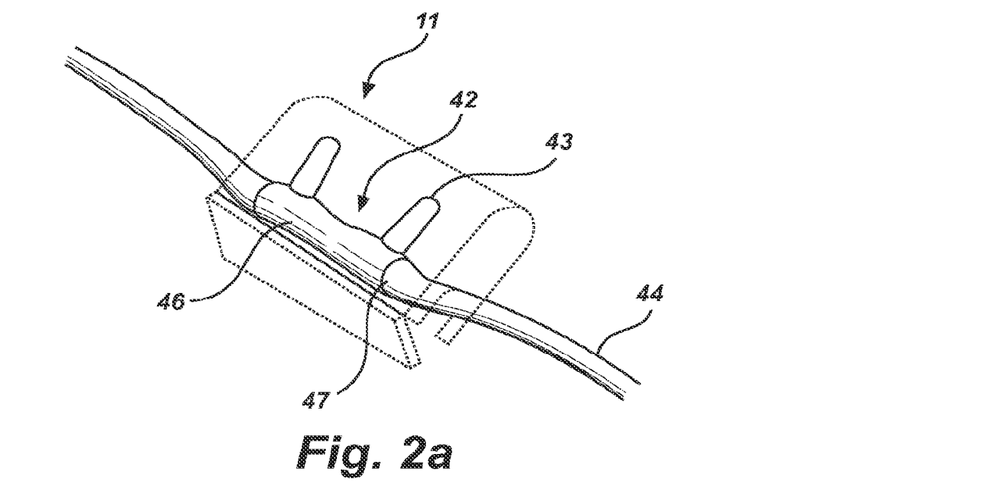
FIG. 2a is a top perspective view of a nasal cannula cover, with a nasal cannula placed therein, according to another exemplary embodiment of the present invention.
Figure 2B:
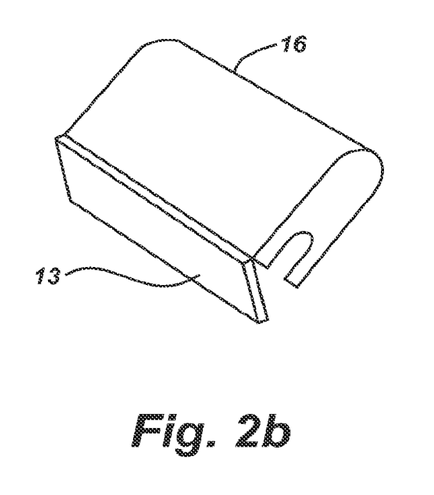
Figure 2C:
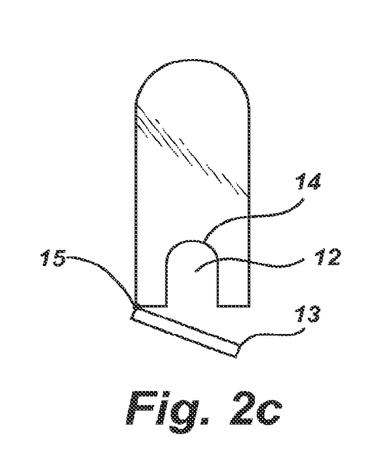
FIG. 2c is a side view of the reusable slide-on cover of FIG. 2b.

Referring now to FIGS. 2a through 2c, a reusable slide-on cover 11 includes a top cover 16 and a hinged closure 13. Both the top cover 16 and the hinged closure 13 are made of semi-rigid plastic material. The top cover 16 has a base tube opening 12 which slides over the cannula feed tube 44. When covering the nasal cannula 42, a half-moon shaped clip 14 can contact the cannula feed tube 44 such that light manual force is required to press the reusable slide-on cover 11 over the cannula feed tube 44. The hinged closure 13 pivots freely on a closure hinge 15. Once the half-moon shaped clip 14 engages the cannula feed tube 44, the patient 45 can manually rotate the hinged closure 13 to cover the base tube opening 12.

Figure 3A:
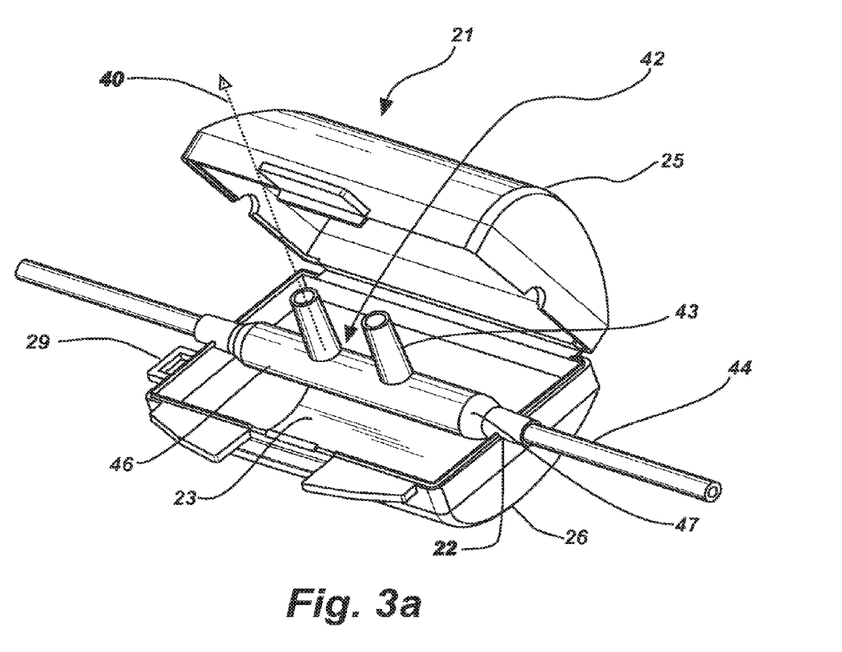
FIG. 3a is a top perspective view of a nasal cannula cover, with a nasal cannula placed therein, according to another exemplary embodiment of the present invention.

Referring now to FIG. 3a, a barrel cover 21 includes a top half 25 and a bottom half 26. When the top half 25 and the bottom half 26 are mated together, the interior space forms an inner cylinder 23, or interior space, which provides clearance between the inner cylinder 23 and the cone shaped prong 43. The barrel cover 21 can rotate 360 degrees around the longitudinal axis of the cannula base tube 46, and the clearance between the cone shaped prong 43 and the inner cylinder 23 will remain. The barrel cover 21 also has a feed tube locator 22 on two sides of the bottom half 26. The feed tube locator 22 contacts the cannula base tube 46 on the nasal cannula 42. The feed tube locator 22 prevents lateral sliding in either direction along the longitudinal axis of the cannula base tube 46. A tether attachment 29 releasably attaches tether members, which are elongated flaccid components that hang the barrel cover at various locations. The tether members can include various quick attachment devices including hooks, snaps, hook & loop, or buttons.

Figure 3B:
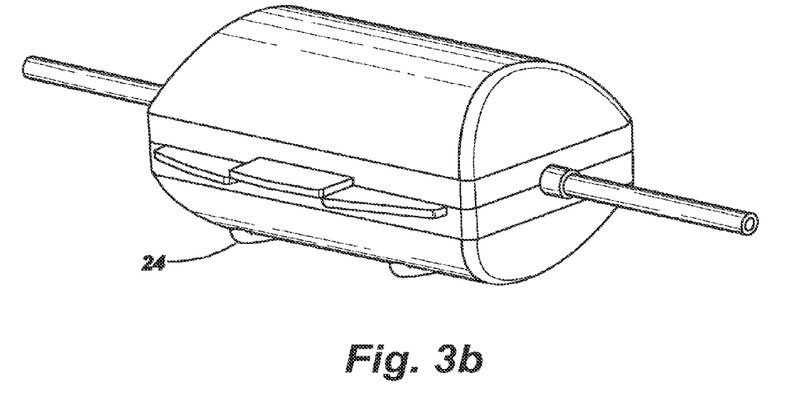

Referring now to FIG. 3b, the barrel cover 21 has one or more leg protrusion 24, or stabilizing member, which provide for setting barrel cover 21 on horizontal surfaces without freely rolling.

Figure 4:
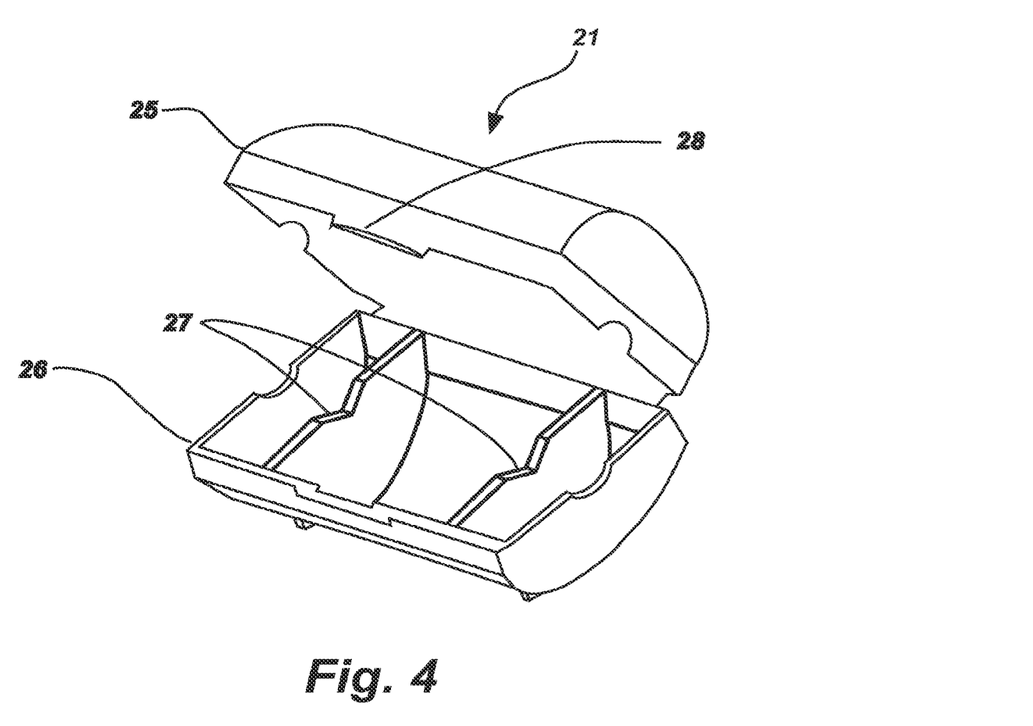
FIG. 4 is a top perspective view of a nasal cannula cover, with a nasal cannula placed therein, according to another exemplary embodiment of the present invention.

Referring now to FIG. 4, the barrel cover 21 can also have a base tube locator 27, or guidance member, on two sides of the bottom half 26. In addition, base tube locator 27 can be added to the top half 25. The base tube locator 27 has, for example, a V-shape which contacts the cannula base tube 46 on the nasal cannula 42. The base tube locator 27 allows misalignment of the nasal cannula 42 to be corrected as the top half 25 approaches the bottom half 26. In addition, FIG. 4 shows a press to open latch 28, or actuating member. The press to open latch 28 can be actuated by compressing the top half 25 with light finger force.

Figure 5A:
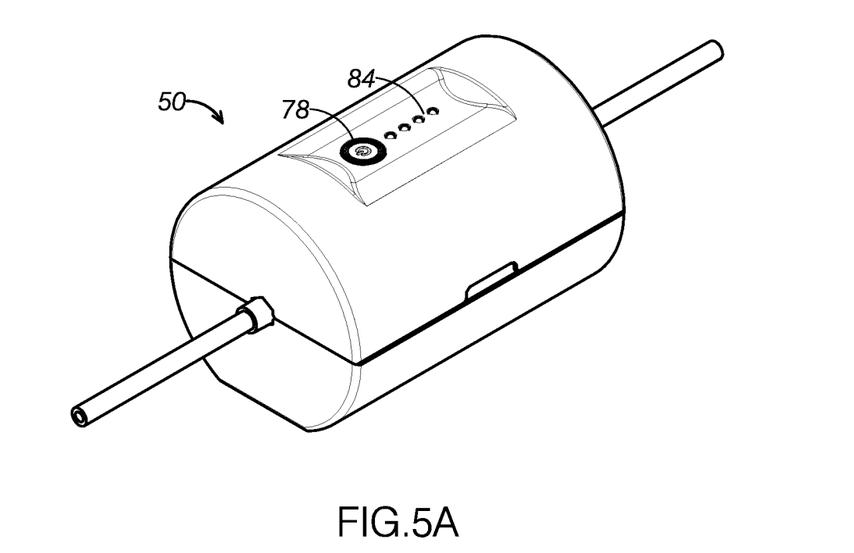
FIG. 5a is a perspective view of a nasal cannula cover, closed, with a nasal cannula placed therein, having a UV light source therewithin, according to another exemplary embodiment of the present invention.
Figure 5B:
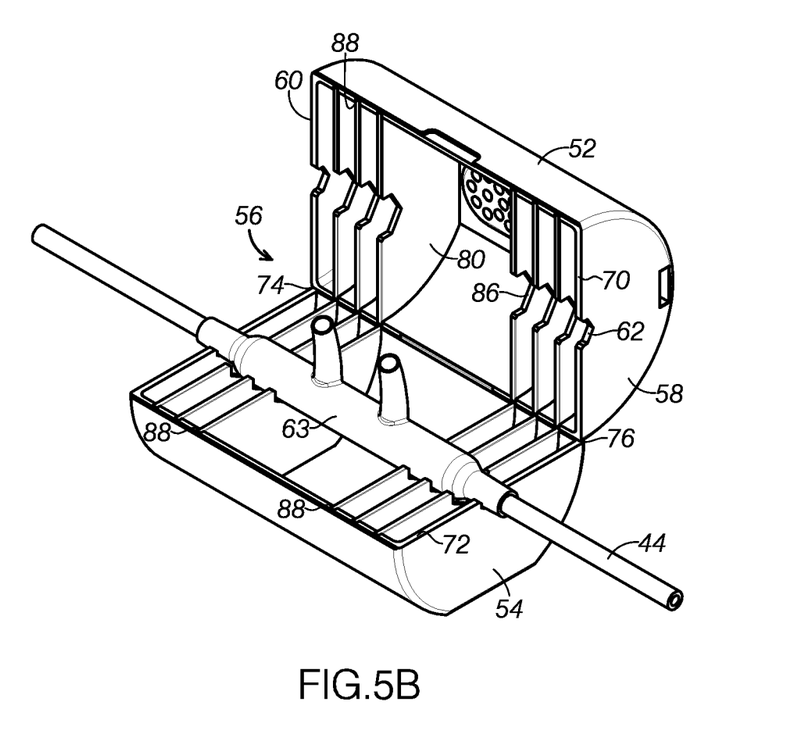
FIG. 5b is a perspective view of the nasal cannula cover of FIG. 5a in an opened configuration.
Figure 5C:
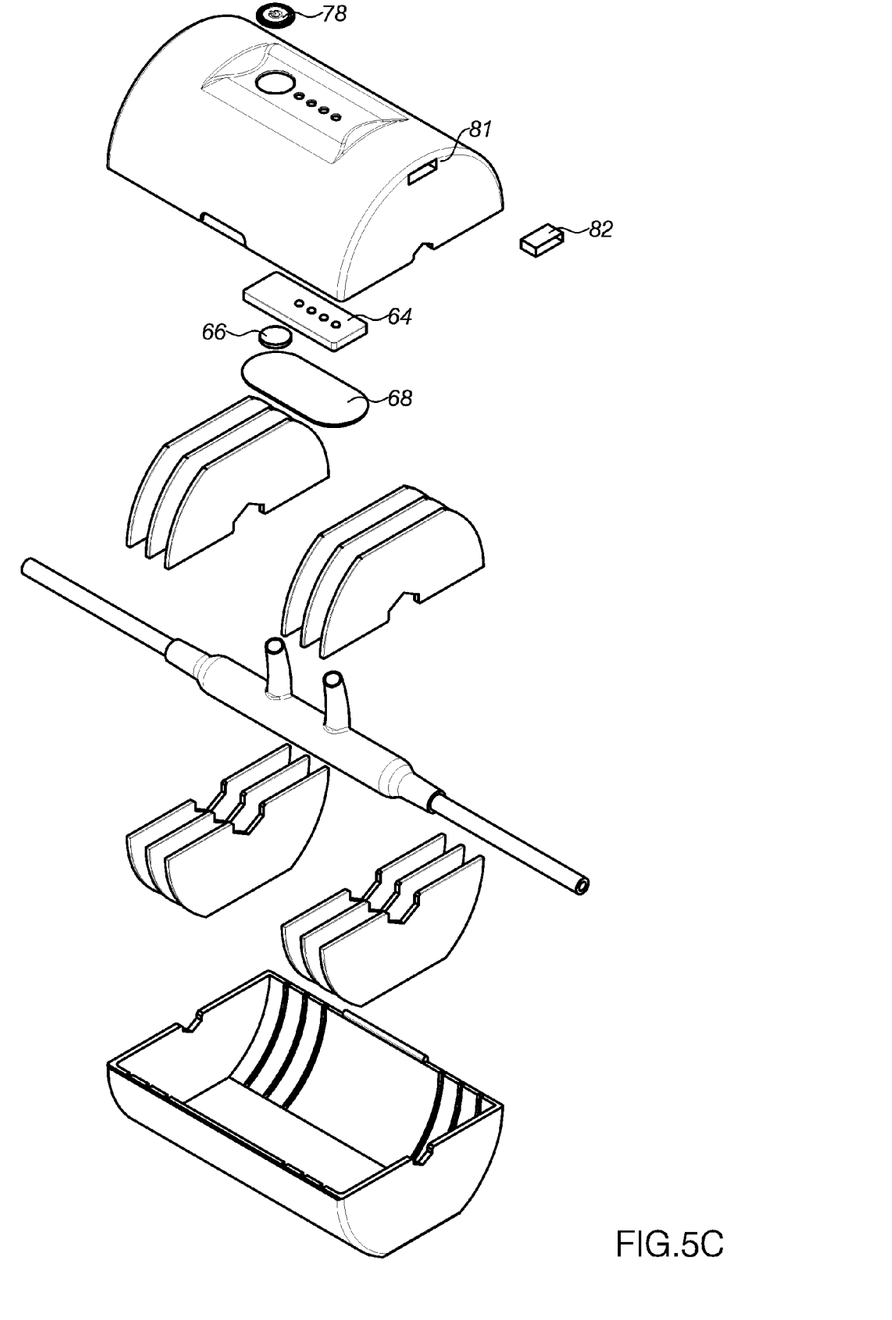

Referring to FIGS. 5a through 5c, in some embodiments, a nasal cannula cover 50 can include a top member 52 and a bottom member 54 that may combine along their top edge 70 and bottom edge 72 to form an enclosed space 56 therebetween. At opposing ends 58, 60 of at least one of the top member 52 and the bottom member 54, openings 62 can be formed that communicates with at least one of the top edge 70 and the bottom edge 72. The openings 62 can be configured to permit the nasal cannula feed tubes 44 to be secured within the openings 62. In some embodiments, the diameter of the openings 62 may create a friction fit with the nasal cannula feed tubes 44 to help prevent the nasal cannula from sliding and/or rotating. In other embodiments, the diameter of the openings 62 may be sized larger than the nasal cannula feed tubes 44 but smaller than the prong base portion 63 of the nasal cannula, thereby preventing sliding of the nasal cannula within the cover, while allowing the prongs to rotate about 360 degrees within the cover 50. While FIG. 5B shows the openings 62 closing on the prong base portion 63 of the nasal cannula, the cover 50 may have a width so that openings 62 close on the nasal cannula feed tubes 44.

Within the enclosed space 56, an ultraviolet (UV) light source 64 can be disposed to emit UV photons toward the nasal cannula prongs 43. The UV light source 64 may include a printed circuit board with the appropriate logic to operate the UV lights. The UV light source 64 may be powered by an internal battery 66, or the nasal cannula cover 50 may include a port 81 to permit an external power source to power the UV light source 64 or to recharge the battery 66. A charge port cover 82 may be disposed in the port 81 when the port is not in use. In some embodiments, a charging base or docking station (not shown) may be used to power the UV light source 64 or charge the battery 66. The UV light source 64 can take various forms and emit UV light in various wavelengths. In some embodiments, the UV light source 64 can be light emitting diodes (LEDs) that emit UV photons. In some embodiments, the UV light source 64 emits UV-C photons. In some embodiments, the UV light source 64 can be disposed inside the nasal cannula cover. In other embodiments, the UV light source 64 can be disposed within or on the exterior of the nasal cannula cover. Regardless of orientation, the UV light source 64 is configured to emit UV photons into the inside (the enclosed space) of the nasal cannula cover. In some embodiments, the UV light source 64 can be disposed within a base station for holding and/or docking the nasal cannula cover. This base station can have a power source, such as an electrical plug, battery, or the like, to power the UV light source. The base station can include a nasal cannula cover retention means to secure the cover to the base station. The retention means may include, for example, one or more frictionally fitting elements, one or more latches, catches, pins or the like that may be released by pressing a release button, thereby freeing the cover from the base station. A detector may be used to detect when the cover is placed in the base station. The detector may be a push button depressed when the cover is secured in the base station or may be a cover sensing mechanism. Regardless of design, the detector may be used to control the UV light source disposed within the base station. A timer may control the time that the UV light source is active. One or more indicator lights may be disposed on the base station. The indicator lights may include a light to identify when the detector detects the cover secured in the base station, a light to identify that the UV light source is in use, a light to show the nasal cannula UV light cycle is complete, and the like. The base station may further include a storage area for storing and/or securing at least a portion of the nasal cannula tubing.

A transparent cover 68 can be disposed to cover the UV light source 64. The cover 68 may also provide a cover for the battery 66 to allow replacement thereof. The cover 68 may also include filters and/or reflectors to scatter the UV photons or permit a predefined wavelength of UV light to enter the enclosed space 56. An open-closed detector 74 can be disposed in the nasal cannula cover 50 to detect when the cover 50 is open or closed. The open-closed detector 74 can be a mechanical detector that detects when the top edge 70 and the bottom edge 72 meet, for example, or may detect rotation of a hinge member 76. In some embodiments, the open-closed detector 74 may be a magnetic detector that may magnetically determine when the cover 50 is opened or closed. The open-closed detector 74 may be used to power the UV light source 64 only when the cover 50 is closed.

In some embodiments, an on/off button 78 may be disposed on an external surface of the case 50 to turn on and off the UV light source 64. The on/off button 78 may also activate a series of lights 84 that can show the battery level, that scroll while the battery is charging, that shows when the UV light is on, and other like functions. The on/off button 78 may have its own light to indicate whether the UV light is on or off.

A view port (not shown) may be provided with a protective lens, for example, to allow a user to look into the closed cover 50 to determine operation of the UV light source 64. Typically, a user will see a glow within the view port when the UV light source 64 is operational One or more feed tube locators, such as ribs 80, may be disposed within the cover 50. The ribs 80 can include cut-outs 86, typically semi-circular cut-outs, that can receive the nasal cannula tubing 44 therein. Typically one rib 80 may be disposed in a rib slot 88 in the top member 52 and another rib 80 may be disposed in a mating rib slot 88 in the bottom member 54, where the two ribs 80 form a typically circular opening when the case 50 is closed. The ribs 80 may come in various sizes to permit retention of various size tubing. Rib slots 88 may be disposed along each side of the case 50 to permit positioning off the ribs 80 in various slots 88. For example, six slots 88 may be disposed in each of the top member 52 and the bottom member 54, as shown in FIGS. 5*b* and 5*c*. Of course, other number of rib slots 88 may be provided. Typically, two ribs 80 are used on a left side of the nasal cannula prongs, and two ribs 80 are used on a right side of the nasal cannula prongs. In some embodiments, the case 50 can be packaged with, for example, six sets of ribs 80 (12 total ribs) and the user may select the appropriately sized rib 80 for their particular nasal cannula. In other embodiments, the case 50 may be packaged with two sets of ribs 80, sized for particular brands of nasal cannulas. In some embodiments, the ribs 80 may be sized to frictionally retain the nasal cannula tubing, prevention rotation of the nasal cannula prongs when the case is closed. In other embodiments, the ribs 80 may align the nasal cannula prongs to prevent contact with the inside surface of the cover when the cover is rotated substantially 360 degrees.

In some embodiments, the ribs 80 may also be used to act as a filter to filter out harmful UV photons so that they do not leak out the openings 62. For example, if a nasal cannula is not in place in the cover 50, the filters will prevent UV photons from escaping out of the cover 50. In some embodiments, the open-closed detector 74 may detect when the nasal cannula is within the cover 50 and only operate the UV light source 64 when the nasal cannula is present. The ribs 80 may also help secure the nasal cannula within the cover 50 and help prevent the prongs 43 from touching the inside thereof.

In some embodiments, at least a portion of the surfaces inside the cover that define the space 56 may be formed from a reflective material designed to reflect UV photons. In this embodiment, the UV photons from the UV light source 64 may be reflected in various manners to help ensure complete coverage of the nasal cannula prongs 43 with UV photons, regardless of the configuration of the nasal cannula inside the cover 50.

Similar to that described above with respect to FIG. 3*a*, the cover 50 can include a tether attachment that releasably attaches tether members, which are elongated flaccid components that be used to hang the cover at various locations. The tether members can include various quick attachment devices including hooks, snaps, hook & loop, buttons or the like.

While FIGS. 5*a* through 5*c* show the UV light source 64, this light source may be provided in any of the above or below described nasal cannula covers or any covers used to cover a nasal cannula.

Figure 6A:
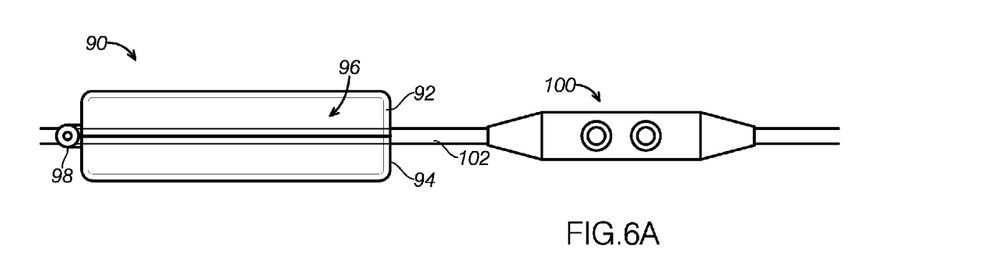
FIG. 6a is a top view of a nasal cannula cover disposed on nasal cannula tubing according to an exemplary embodiment of the present invention.
Figure 6B:
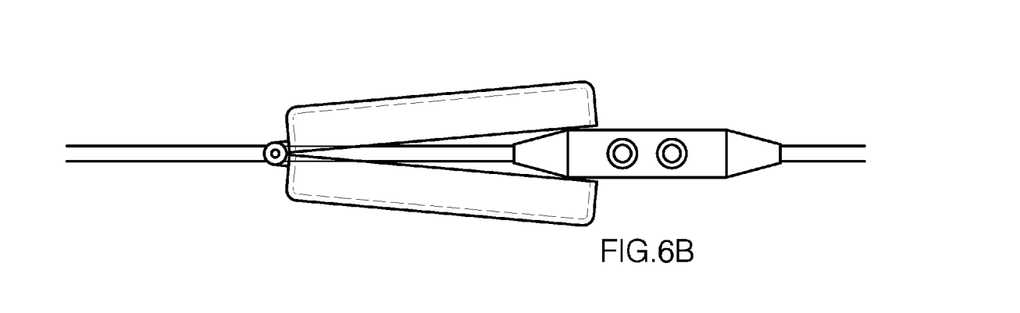
FIG. 6b is a top view of the nasal cannula cover of FIG. 6a, opened to insert and/or remove the nasal cannula prongs.
Figure 6C:
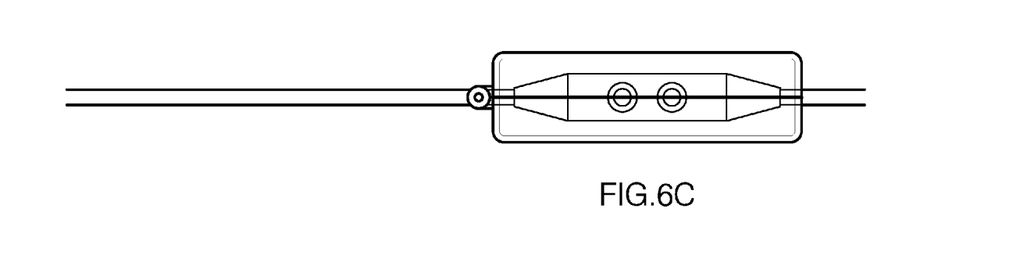
FIG. 6c is a top view of the nasal cannula cover of FIG. 6a, with the nasal cannula prongs encased therein.

Referring now to FIGS. 6*a* through 6*c*, a nasal cannula cover 90 can include a top member 92 that closes against a bottom member 94 with an enclosed space 96 therebetween. A hinge 98 may be used to permit opening and closing of the cover 90. In some embodiments, the hinge 98 may urge the top and bottom members 92, 94 in a closed position that can be resiliently opened as desired.

As shown in FIG. 6*b*, a user may open the top member 92 from the bottom member 94 and slide the cover 90 to encase the nasal cannula prongs 100. The cover 90 may be slidably disposed on a portion of the nasal cannula tubing 102, as shown in FIG. 6*a*. In some embodiments, the top and bottom members 92, 94 may separate sufficiently to permit the cover 90 to be applied to and removed from the tubing 102.

Figure 7A:
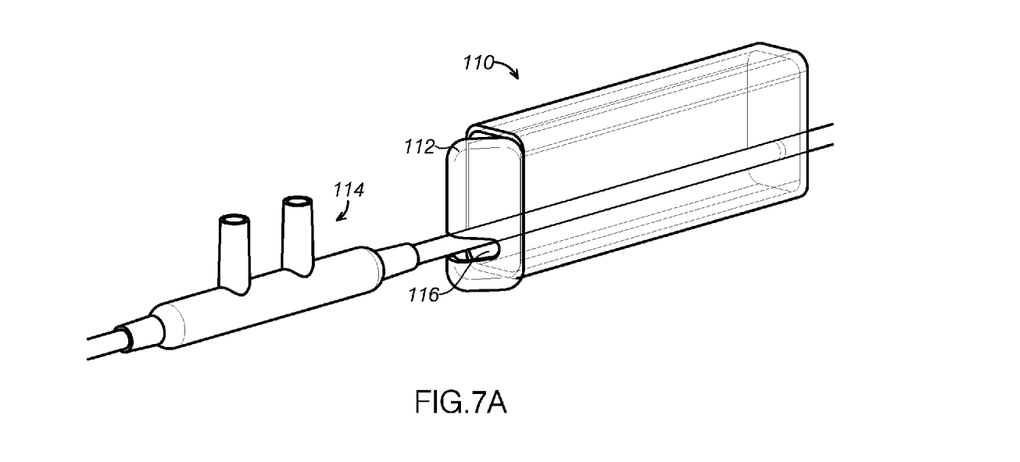
FIG. 7a is a perspective view of a nasal cannula cover having an end door according to an exemplary embodiment of the present invention.
Figure 7B:
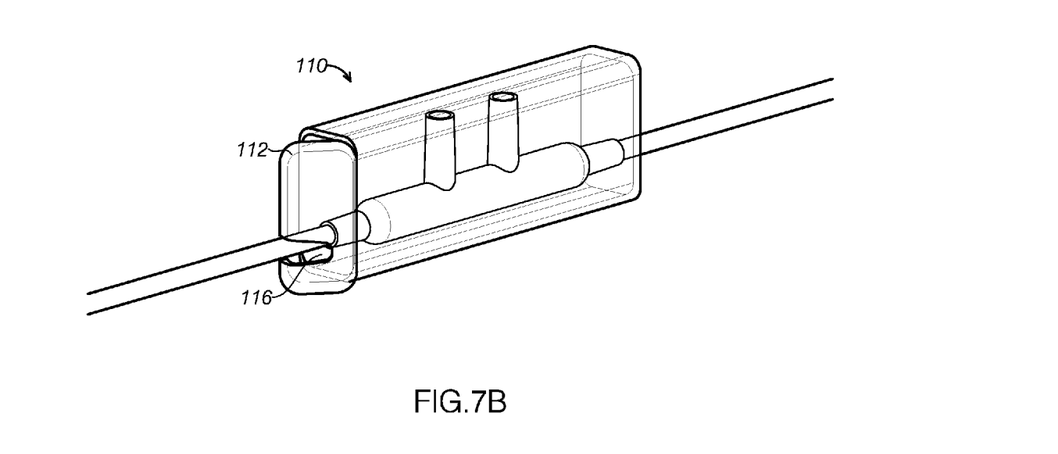
FIG. 7b is a perspective view of the nasal cannula cover of FIG. 7a, with the nasal cannula prongs encased therein.

Referring to FIGS. 7*a* and 7*b*, a nasal cannula cover 110 may have a hinged component, such as a hinged door 112, on at least one end thereof to permit the prongs 114 of the nasal cannula to be stored inside the cover 110. The door 112 may have a slot 116 to permit the door to close with the prongs 114 inside.

Figure 7C:
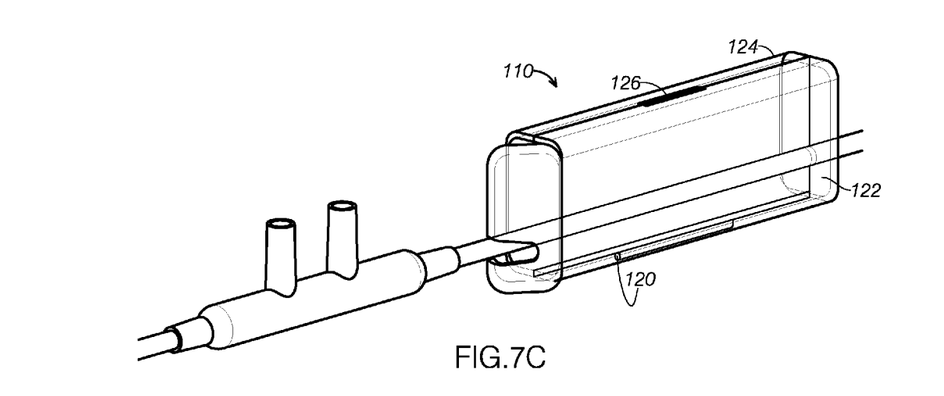

In some embodiments as shown in FIG. 7*c*, the cover 110 of FIG. 7*a* (or the cover 90 of FIG. 6*a*) may include a hinge 120 to permit a first side 122 to be hingedly connected to a second side 124, thereby allowing removal of the cover 110. A latch 126 may be used to hold the sides 122, 124 in the closed configuration. The hinge 120 may take various forms such as, for example, a living hinge. While FIG. 7*c* shows the sides 122, 124 as being forward and rearward sides, the sides could open and close from top to bottom. In this embodiment, the door 112 may hinge from the top of bottom, rather than the side, as shown.

Figure 7D:
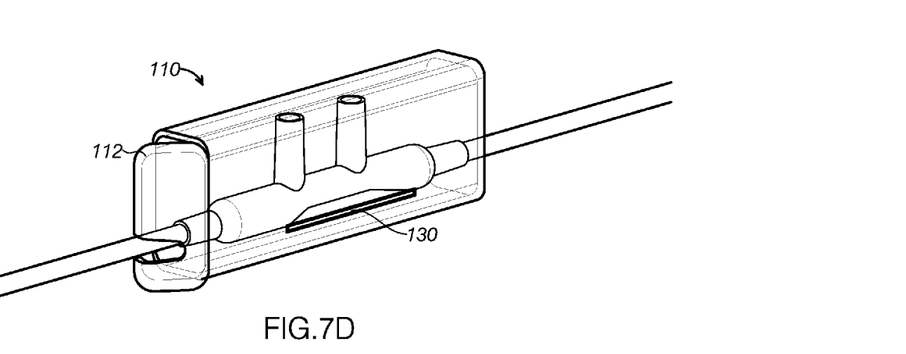
Figure 7E:
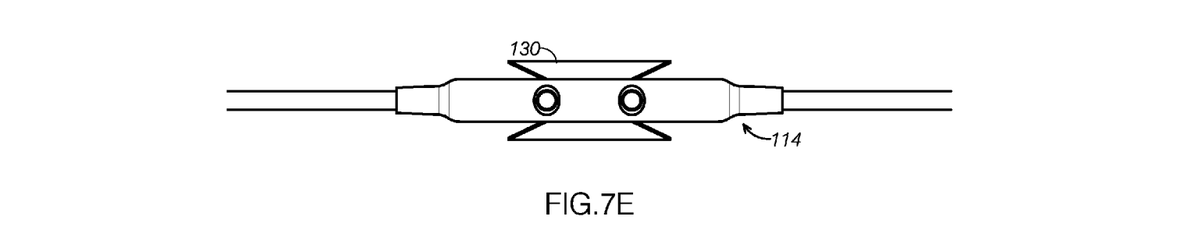
FIG. 7e is a top view of the rotation resistance structure of FIG. 7d.

Referring to FIGS. 7*d* and 7*e*, the cover 110 of FIG. 7*a* (or the cover 90 of FIG. 6*a*) may include a rotation limiting feature 130 that may prevent rotation of the nasal cannula prongs 114. This rotation limiting feature 130 may take various forms. For example, the rotation limiting feature 130 may include protrusions on sides of the cover to press against the base of the nasal cannula prongs 114 to prevent rotation thereof. This feature may keep the nasal cannula prongs 114 from touching the inside of the cover 110.

Figure 8A:
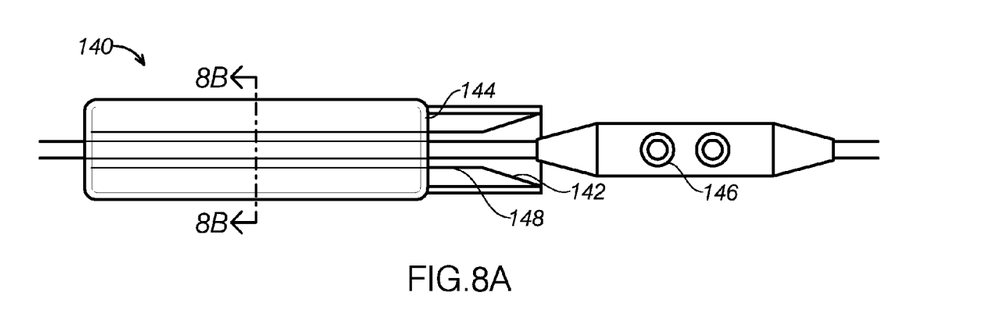
FIG. 8a is a top view of a nasal cannula cover having a prong alignment feature.
Figure 8B:
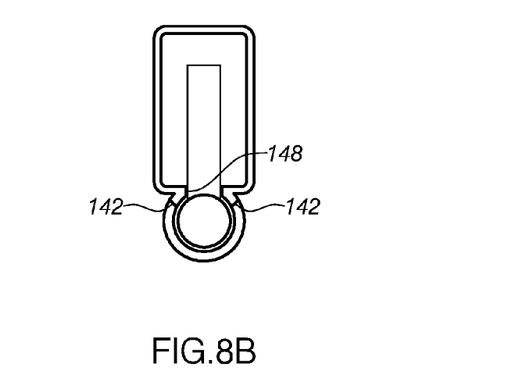

Referring now to FIGS. 8*a* and 8*b*, a nasal cannula cover 140 may include a cam surface 142 that helps guide the nasal cannula therein with the nasal cannula prongs 146 prevented from touching the inside of the cover 140. The cam surface 142 can guide and align the nasal cannula prongs 146 and a cam slot 148 can help prevent rotation of the nasal cannula prongs 146 when disposed inside to cover 140. A door 144 can open and close to allow insertion and removal of the nasal cannula prongs 146. This cam surface design may be applied to many of the above described designs and the UV light source discussed above may be used in this embodiment.

Figure 9:
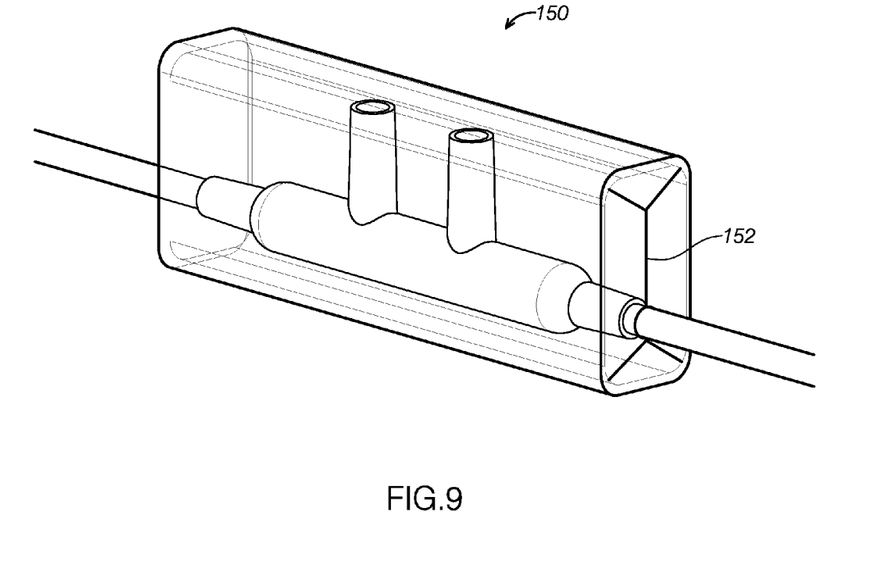
FIG. 9 is a perspective view of a nasal cannula cover having a cut slot in a flexible membrane for insertion of a nasal cannula therein.

Referring to FIG. 9, in place of a door, as described above, the nasal cannula cover 150 can include a slit 152 cut in one or both sides to allow insertion of the nasal cannula prongs therein. The slit 152 can be resiliently opened by inserting the nasal cannula prongs inside the cover 150. The slit 152 can be designed to automatically close about the nasal cannula to protect the nasal cannula prongs stored therein.

It should be understood, of course, that the foregoing relates to exemplary embodiments of the invention and that modifications may be made without departing from the spirit and scope of the invention as set forth in the following claims.

What is claimed is:

1. A method for protecting prongs of a nasal cannula when not in use, comprising:
   placing the prongs of the nasal cannula into a space inside a nasal cannula cover;
   directing nasal cannula tubing into openings formed on opposite sides of the nasal cannula cover; and
   closing the nasal cannula cover to secure the prongs within the space.

2. The method of claim 1, further comprising securing the nasal cannula inside the cover to prevent a distal end of the prongs of the nasal cannula from contacting an inside surface of the nasal cannula cover.

3. The method of claim 1, wherein protrusions hold a prong base portion of the prongs of the nasal cannula to limit rotation of the prongs when disposed inside the space.

4. The method of claim 1, further comprising permitting the prongs to rotate substantially about 360 degrees without contacting an inside surface of the nasal cannula cover.

5. The method of claim 1, further comprising sterilizing the prongs of the nasal cannula with ultraviolet photons emitted from an ultraviolet light source.

6. The method of claim 1, wherein the ultraviolet light source is disposed inside the nasal cannula cover.

7. The method of claim 1, wherein ribs are disposed on each side of the prongs of the nasal cannula, the ribs having a rib opening sized to permit tubing of the nasal cannula to pass therethrough.

8. The method of claim 7, wherein the ribs insert into rib slots formed in the nasal cannula cover.

9. The method of claim 7, wherein the ribs include first and second ribs disposed on either side of the prongs of the nasal cannula.

10. The method of claim 8, wherein the rib slots include a plurality of rib slots inside the space on each side of the nasal cannula cover.

11. The method of claim 1, wherein the nasal cannula cover is assembled integrally with and slides along nasal cannula tubing of the nasal cannula.

12. The method of claim 11, further comprising opening a hinged component on the nasal cannula cover to permit placement within and removal from the nasal cannula cover.

* * * * *